Figure 1:
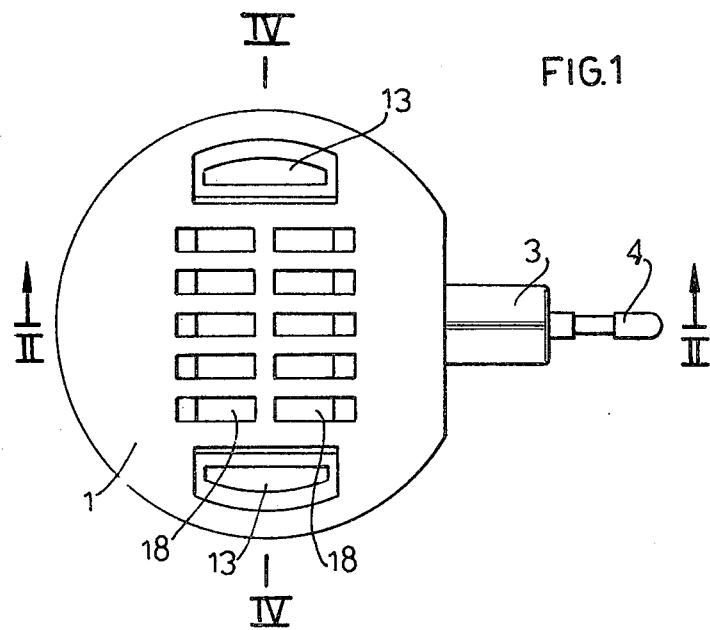

United States Patent [19]

Zobele

[11] Patent Number: 4,467,177

[45] Date of Patent: Aug. 21, 1984

[54] HEATING DEVICE FOR TABLETS CONTAINING EVAPORABLE SUBSTANCES AT DIFFERENT TEMPERATURES

[75] Inventor: Fulvio Zobele, Trento, Italy

[73] Assignee: Zobele Industrie Chimiche S.p.A., Trento, Italy

[21] Appl. No.: 471,194

[22] Filed: Mar. 1, 1983

[30] Foreign Application Priority Data

Mar. 26, 1982 [IT] Italy ............................... 21356/82[U]

[51] Int. Cl.³ ................................................ A61L 9/03
[52] U.S. Cl. ................................... 219/271; 219/521;
219/276; 43/129
[58] Field of Search ................................. 219/271–276,
219/521, 436, 214, 457–459; 43/128–130, 125;
239/135, 133, 128, 34, 51.5, 47, 53–60; 206/0.5;
422/305, 306, 125; 221/150 R, 150 A

[56] References Cited

U.S. PATENT DOCUMENTS

| | | | |
|---|---|---|---|
| 2,611,068 | 9/1952 | Wellens | 219/272 |
| 2,942,090 | 6/1960 | Diehl | 219/271 |
| 4,251,714 | 2/1981 | Zobele | 219/275 |
| 4,391,781 | 7/1983 | VanLit | 219/274 |

FOREIGN PATENT DOCUMENTS 2071497  9/1981  United Kingdom .................. 43/129

Primary Examiner—Roy N. Envall, Jr.
Assistant Examiner—Teresa J. Walberg
Attorney, Agent, or Firm—John S. Hale

[57] ABSTRACT

A heating device included a body having a seat for the positioning of at least one heating support having inserted therein at least one electrical resistive element, the resistive element being electrically connected to the pins of a plug for insertion into an electric socket. The body is provided with a first slit for the positioning of a first small plate or tablet, containing evaporable substances (such as antifly and antimosquito substances), so as to bring it in contact with at least a portion of the heating support and cause the evaporation of the substances in the tablet at a high temperature (about 140° C.). A further seat is also provided spaced from the heating support, in which a support is arranged for a second tablet (for example, containing deodorizing substances), which evaporate at a not unduly high temperature (about 70° C.). The body provides apertures for the passage and diffusion of the evaporated substances. Additionally, the plug pins are arranged on a support adapted to rotate through a 90 degree arc, so that the tablet can be inserted always in a horizontal position, regardless of orientation of the holes of the electric socket.

7 Claims, 4 Drawing Figures

HEATING DEVICE FOR TABLETS CONTAINING EVAPORABLE SUBSTANCES AT DIFFERENT TEMPERATURES

This invention relates to a heating device for tablets containing substances evaporable at different temeperatures. The prior art heating devices provide a containing body provided with apertures at the heating support. Such are generally made with a metal base plate beneath which a heating resistance is applied. Said support could also be made of insulating material, in which a fully insulated electrical resistance is positioned. This last solution has been already patented by the applicant.

Further solutions provide that said support features a flat heated surface for supporting a tablet containing, for example insecticidal or deodorizing substances, which evaporate when heated to a given temperature. However, should the tablet contain a deodorizing substance, it often occurs that the temperature achieved by the flat surface is much higher than that required for obtaining a deodorizing effect of rather low intensity, but extended in time.

Therefore, it is the object of the present invention to provide a device which, depending on requirements, accomplishes either the evaporation of substances in an insecticidal tablet, heated to a high temperature (about 140° C.), or the evaporation of substances in a deodorizing tablet, heated to a lower temperature (about 70° C.).

The above mentioned object is achieved by providing in the containing body of the device, in addition to the standard seat for an insecticidal tablet which is to be heated to a high temperature, a second additional seat located at some distance from the heating support, for evaporation at a lower temperature of a substance contained in the deodorizing tablet, which are heated by convection.

The present invention also provides that, at the additional seat, apertures are provided on the containing body for diffusion of the evaporated substance.

Another solution provides that the body is formed by two parts engaging support of electrical plug pins. Particularly, said parts forming the body are freely rotatable about the pin support.

A further solution envisages the provision of stop elements for blocking the rotation of said body past an angle exceeding 90°.

A particular modified embodiment envisages an additional or auxiliary flat support which is provided with apertures to aid the convection heating of the tablets.

Figure 2:
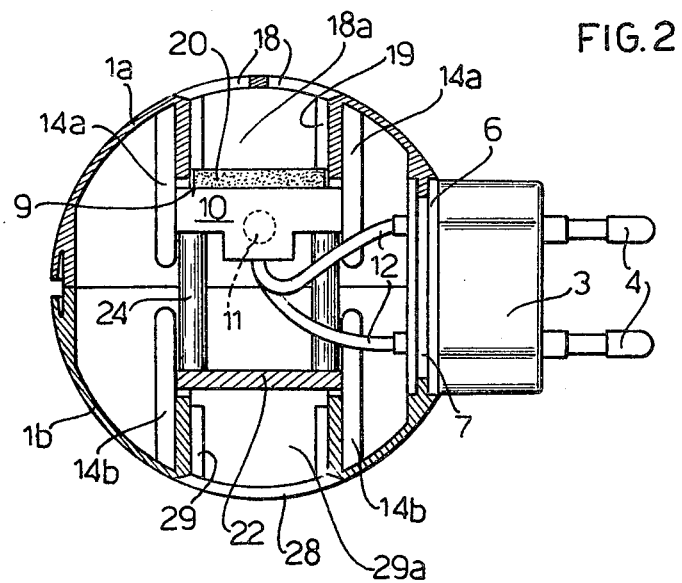
Figure 3:
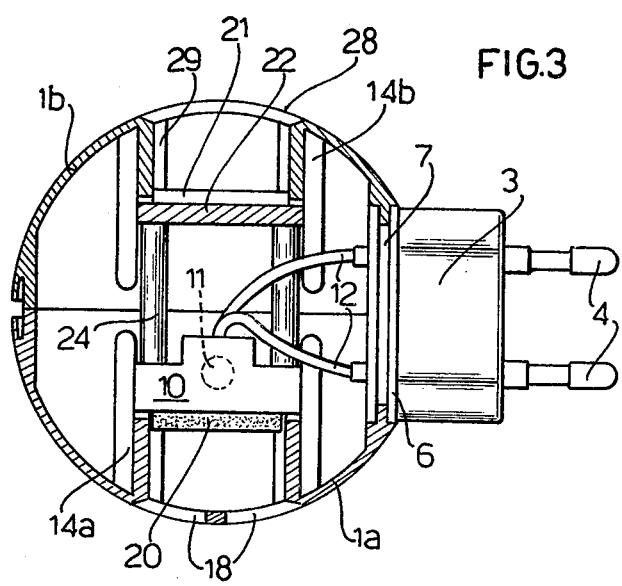
Figure 4:
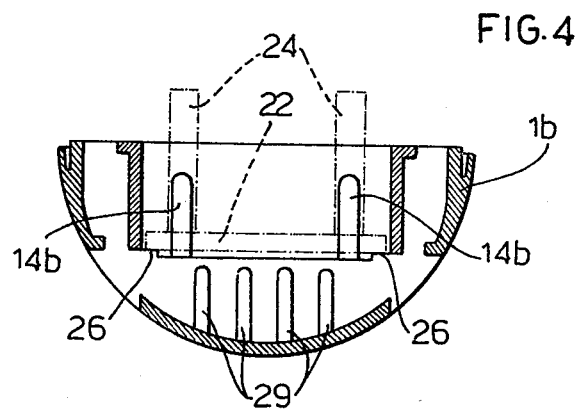

The invention will now be illustrated with reference to the accompanying drawings, in which:

FIG. 1 is a front view of the device;
FIG. 2 is a sectional view of the device taken along lines II—II of FIG. 1;
FIG. 3 is a view showing the device as rotated through 180° with respect to the position of FIG. 2; and
FIG. 4 is a fragmentary sectional view taken along lines IV—IV of FIG. 1.

As shown in the figures of the accompanying drawings, a device according to the present application essentially includes a containing body 1 comprising two parts, 1a and 1b, preferably of a different color and engaged as conventionally known. Such parts engage with a support 3 for pins 4 providing a poles of a plug to be inserted in the voltage socket. The pin support 3 terminates with a collar 6 provided with a groove 7. Said support 3 has the two parts 1a and 1b engaged therein to be freely rotatable thereabout. Projections 14a are provided in said body for engaging heating support 10, in which an insulated electrical resistance 11 is positioned. The ends of said resistance are connected by connecting wires 12 to said pins 4. The body 1 is provided with apertures 18 for air passage within a cavity 18a fitted with projections 19. The heating support 10 is provided with a flat face 9, on which a tablet 20 is brought to bear and retained thereto by said projections 19. It is inserted via the slits 13 in the body.

During operation, as tested, the upper face 9 of this heating support 10, for example made of ceramics, achieves a temperature of about 140° C., which is normally the temperature required for optimum evaporation of standard antimosquito and antifly tablets.

However, this temperature is too high for tablets such as those impregnated with deodorizing substances, where it is desired to provide a less intense perfume and an extended duration, of deodorizing effect. To this end, an auxiliary flat support 22 is provided for engagement with projections 14b and bearing against abutments 26 (FIG. 4) provided with apertures 80 for promoting convection transmission of heat and on which a further tablet 21 can be positioned. This flat support 22 has legs 24 that, in the body assembly, bear against said heating support 10. Said tablet can be inserted through the slit in the body and retained by the projections 29. Provision is also made for apertures 28 for ambient diffusion of the substances evaporated from the tablet inserted in the seat.

Thus, the evaporable tablet no longer receives heat by direct contact, but by convection. The substances evaporated at an average temperature of about 70° C., to obtain a deodorizing effect which is less intense, but more extended in time.

The device can also be simultaneously used for release of insecticide and deodorant. Thus, two tablets can be simultaneously inserted; namely, one tablet placed in direct contact with the heating device and another tablet on the auxiliary flat support 10 for convective heating. In order to enable a correct positioning thereof in the apparatus, said body 1 is rotatable around collar 6. In this solution, stop means 70 are provided for preventing any rotation exceeding 90°. This enables tablet insertion in a horizontal position for socket holes arranged both vertically and horizontally.

What I claim is:

1. A heating device for tablets containing substances evaporable at different temperatures, including a body provided with a pin support, a plurality of electric plug pins mounted to said pin support and adapted to be inserted in a voltage socket, and with a first seat for positioning of at least one heating support of insulating material, in which at least one electrical heating element is positioned, the ends of which are connected respectively to the pins, said body being provided with at least one slit for the positioning of an evaporable tablet at a first distance from said heating element, and comprising means for providing at least one additional seat for the positioning of at least one further tablet at a second distance from said heating element greater than said first distance.

2. A device according to claim 1, wherein said means for providing at least one additional seat are arranged at a predetermined spacing relative to the heating support to obtain a temperature at said first seat about 70 degrees C. greater than a temperature at said at least one additional seat.

3. A device according to claim 1, wherein said additional seat has arranged therein an additional plane for supporting said at least one further tablet.

4. A device according to claim 1, wherein at the tablet seats, apertures are provided on the body for the passage of vapor from said evaporable tablet.

5. A device according to claim 1, wherein said body comprises at least two body parts engaging with said pin support, said two body parts being freely rotatable around said support.

6. A device according to claim 4, wherein said at least one additional seat for the positioning of at least one further tablet is provided with apertures for the passage of heat being transmitted by convection from said heating element.

7. A device according to claim 5, wherein stop elements are provided for preventing said two body parts from rotating through an angle exceeding 90 degrees.

* * * * *